United States Patent
Harms et al.

(10) Patent No.: US 9,638,647 B2
(45) Date of Patent: May 2, 2017

(54) METHOD FOR DETERMINING THE RETENTION CAPACITY OF FUEL VAPOR FILTERS

(71) Applicant: Kautex Textron GmbH & Co. KG, Bonn (DE)

(72) Inventors: Daniel Harms, Siegburg (DE); Volker Treudt, Windeck (DE)

(73) Assignee: Kautex Textron GmbH & Co. KG, Bonn (DE)

( * ) Notice: Subject to any disclaimer, the term of this patent is extended or adjusted under 35 U.S.C. 154(b) by 339 days.

(21) Appl. No.: 14/403,335

(22) PCT Filed: May 23, 2013

(86) PCT No.: PCT/EP2013/060576
§ 371 (c)(1),
(2) Date: Nov. 24, 2014

(87) PCT Pub. No.: WO2013/174900
PCT Pub. Date: Nov. 28, 2013

(65) Prior Publication Data
US 2015/0153291 A1    Jun. 4, 2015

(30) Foreign Application Priority Data

May 24, 2012  (DE) .......................... 10 2012 010 241

(51) Int. Cl.
*G01N 25/00*      (2006.01)
*F02M 25/08*      (2006.01)
(Continued)

(52) U.S. Cl.
CPC ............. *G01N 25/00* (2013.01); *F02M 25/08* (2013.01); *F02M 25/089* (2013.01);
(Continued)

(58) Field of Classification Search
CPC .... G01N 25/00; F02M 25/08; F02M 25/0854; F02M 25/089; G01M 15/042; G01M 15/02
(Continued)

(56) References Cited

U.S. PATENT DOCUMENTS

| | | | |
|---|---|---|---|
| 4,951,643 A * | 8/1990 | Sato .................... | F02M 25/0836 |
| | | | 123/519 |
| 5,243,944 A | 9/1993 | Blumenstock | |

(Continued)

FOREIGN PATENT DOCUMENTS

| | | |
|---|---|---|
| DE | 4243250 A1 | 6/1994 |
| EP | 0528339 B1 | 5/1996 |

OTHER PUBLICATIONS

English language PCT International Search Report mailed Oct. 21, 2013, received in corresponding PCT Application No. PCT/EP13/60576, 4 pgs.

(Continued)

*Primary Examiner* — Daniel S Larkin
*Assistant Examiner* — Anthony W Megna Fuentes
(74) *Attorney, Agent, or Firm* — Grossman Tucker Perreault & Pfleger, PLLC

(57) ABSTRACT

The invention relates to a method of determining the retention capacity of fuel vapor filters for motor vehicles, wherein a temperature profile of the fuel is recorded on a motor vehicle in a SHED chamber during a temperature cycle. A fuel vapor volumetric flow for a temperature change is calculated from the temperature profile. In a measurement arrangement (1) fuel is evaporated by means of an evaporator (2) and is output by means of a charging pump (9) to a fuel vapor filter (4) disposed in an oven (5). The bleed emissions of the fuel vapor filter (4) are measured at least during the charging.

13 Claims, 2 Drawing Sheets

(51) Int. Cl.
  *G01M 15/04* (2006.01)
  *G01M 15/02* (2006.01)
(52) U.S. Cl.
  CPC ...... *F02M 25/0854* (2013.01); *G01M 15/042* (2013.01); *G01M 15/02* (2013.01)
(58) Field of Classification Search
  USPC .................. 73/114.38–114.39; 123/518–519
  See application file for complete search history.

(56) References Cited

U.S. PATENT DOCUMENTS

| | | | |
|---|---|---|---|
| 5,273,020 A | 12/1993 | Hayami | |
| 5,427,076 A | 6/1995 | Kobayashi et al. | |
| 5,592,372 A * | 1/1997 | Artail | G01M 17/007 700/73 |
| 6,279,548 B1 | 8/2001 | Reddy | |
| 8,529,659 B2 | 9/2013 | Streib et al. | |
| 2010/0300405 A1* | 12/2010 | Uhrich | F02B 33/40 123/435 |
| 2012/0095631 A1 | 4/2012 | Rauner | |

OTHER PUBLICATIONS

English language PCT Written Opinion mailed Oct. 21, 2013, received in corresponding PCT Application No. PCT/EP13/60576, 5 pgs.

\* cited by examiner

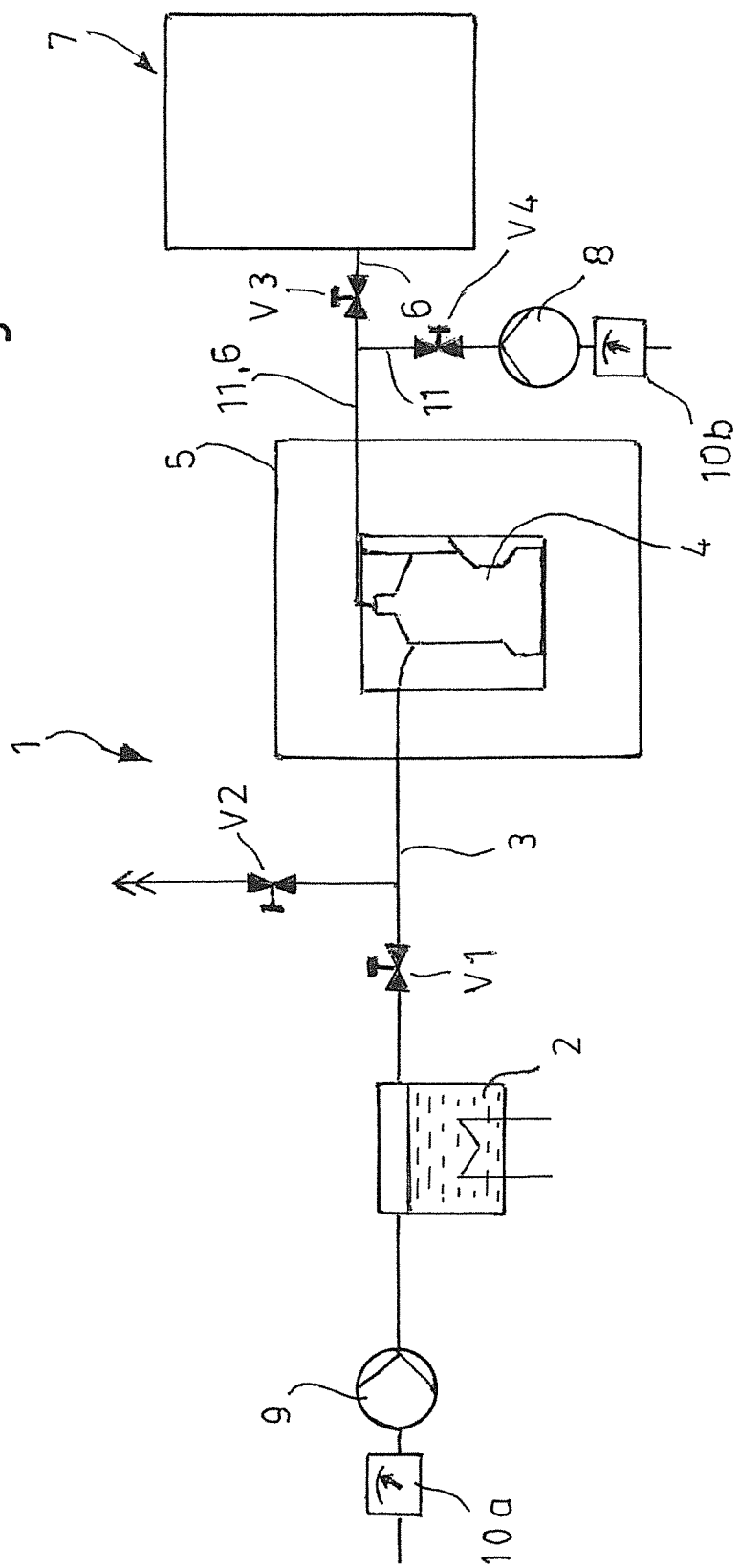

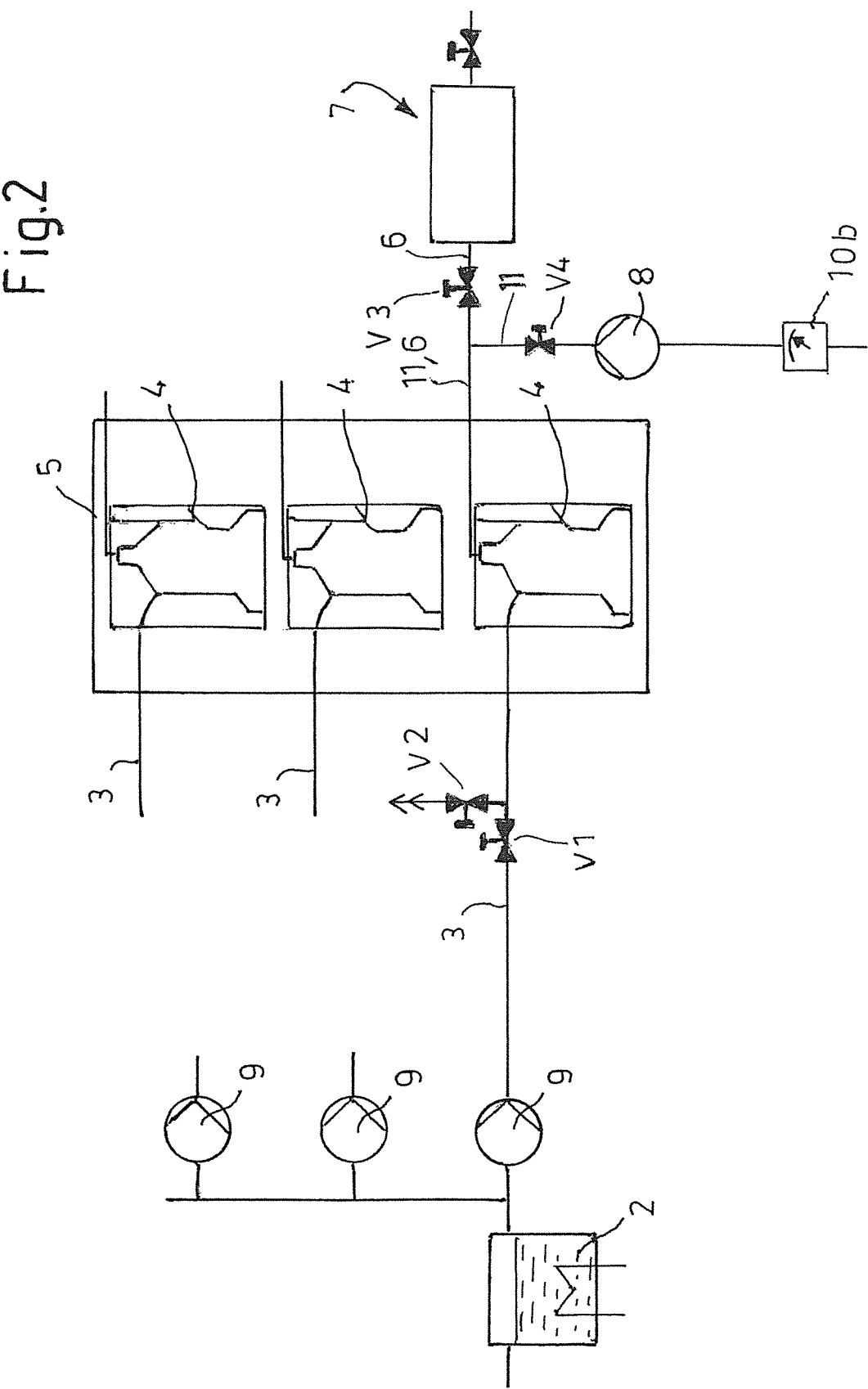

METHOD FOR DETERMINING THE RETENTION CAPACITY OF FUEL VAPOR FILTERS

Methods for determining the retention capacity of fuel vapor filters for motor vehicles are also known as so-called SHED Tests (Sealed Housing for Evaporation Determination). Complete motor vehicles and individual components of the fuel system of the motor vehicles are subjected to such SHED tests. The use of so-called SHED chambers for this purpose is known, which are generally in the form of chambers of quadrilateral cross-section with stainless steel cladding. Said chambers can be closed gas tight and can be provided with a temperature control means, an air circulation housing and a means for analyzing the expelled air. The size of SHED chambers is usually dimensioned so that a motor vehicle can be fully accommodated by such a climate-controlled chamber.

Fuel systems of motor vehicles with OTTO engines usually comprise, besides the fuel tank and a means of delivering fuel to the internal combustion engine of the motor vehicle, also at least one fuel vapor filter, which represents the interface between the fuel tank system and the atmosphere. Ventilation of the fuel tank usually takes place via the fuel vapor filter, which is usually made in the form of an active carbon filter and thus of course has only a limited charge capacity. Because there is not unlimited installation space in the motor vehicle for the disposition of a fuel vapor filter, the dimensioning and design of the fuel vapor filter have a decisive influence. Fuel vapor filters are thus likewise subjected to so-called SHED tests under standard conditions with the aim of determining the retention capacity of the fuel vapor filter. For this purpose the fuel tank filled with fuel is placed inside a SHED chamber, the venting port of the fuel vapor filter is connected to a collecting container, which in turn is connected to a means of hydrocarbon detection, e.g. to a flame ionization detector. Then a specified temperature profile is traversed inside the SHED chamber over one or a plurality of cycles, e.g. over a number of days with the aim of determining the so-called "bleed emissions" or "diurnal bleed losses" of the fuel vapor filter. These are those hydrocarbon emissions that are given off to the atmosphere by the fuel vapor filter with the vehicle stationary as a result of temperature fluctuations in the surroundings of the motor vehicle. Heating up of the fuel tank causes increased transition of hydrocarbons into the gas phase and thus an increase in the volume of the gas in the gas collection chamber/compensating volume of the fuel tank with the result that charging of the fuel vapor filter takes place. With decreasing temperature this process takes place in the opposite direction, i.e. the fuel vapor filter absorbs air from the surroundings and gaseous hydrocarbons in the compensating volume of the container change into the liquid phase. Sometimes so-called "bleed emissions" are thereby released via the venting port of the fuel vapor filter.

There are countless known attempts and measures for improving the repetition accuracy of SHED measurements, because the measurement results of SHED tests for repeated measurements frequently have a relatively large scatter range, even for approximately constant boundary conditions. There are diverse error sources, e.g. the evaporation of fuels in the SHED chamber causes absorption effects.

Moreover, it is known that different measurement results can also be caused by fluctuations of the fuel charge.

The known methods are somewhat laborious, insofar as they can only be carried out in parallel under difficult circumstances with a plurality of fuel vapor filters. For this purpose it is necessary to install a plurality of measurement arrangements inside a chamber.

The object of the invention is to provide a method for determining the retention capacity of fuel vapor filters for motor vehicles, which is simplified and has improved repetition accuracy. Moreover, acceleration of the SHED tests is also to be possible.

The object of the invention is finally to provide a suitable test arrangement.

The object forming the basis of the invention is achieved with a method for determining the retention capacity of fuel vapor filters for motor vehicles, wherein the method comprises the following process steps:

a) Disposing an at least partly fuelled motor vehicle in a heatable test environment, b) Heating the test environment of the motor vehicle from a specified initial temperature to a specified target temperature during a specified time interval, c) Measuring the fuel temperature during the heating and determining and recording a temperature profile, d) Calculating a theoretical volume of hydrocarbon vapor for the temperature change over the entire temperature cycle according to step b) or setting an empirically determined volume of hydrocarbon vapor for the temperature change over the entire temperature cycle according to step b), e) Evaporating a volume of fuel, f) Disposing at least one fuel vapor filter conditioned for test purposes in a heatable container, g) Heating the container to the target temperature from step b) with simultaneous charging with the evaporated volume of hydrocarbon vapor until reaching the theoretical volume of hydrocarbon vapor calculated according to step d) or an empirically determined volume of hydrocarbon vapor, h) Cooling the container to the initial temperature while discharging the fuel vapor filter with a flushing air volume flow that corresponds to the charging volume flow according to step g), i) Determining the hydrocarbon emissions at the outlet of the fuel vapor filter during the charging and j) possibly repeating process steps g) through i).

The invention is based on the knowledge that the hitherto known SHED chamber tests are especially affected by the disadvantage that indirect and extremely sluggish fuel temperature control takes place inside the SHED chamber. The applicant has determined with experimental measurements that the actual fuel temperature inside the fuel tank, measured there with temperature sensors, always significantly lags behind or follows in time the measured temperatures at different points in the SHED chamber. Using various temperature recordings by means of sensors disposed inside the SHED chamber and by means of sensors disposed within the fuel the applicant was able to determine that the temperature inertia of the fuel tank system disposed in the chamber is so great that it has a significant influence on the repetition accuracy of the SHED measurements, especially being dependent on the placement of the fuel tank within the SHED chamber.

Such an experiment according to the prior art is not realistic because the fuel tank in the SHED chamber is subject to a temperature variation regardless of its installation situation on the motor vehicles and therefore in this respect is not realistic.

According to the application it is therefore proposed that the entire motor vehicle with the filled fuel tank is subjected to a temperature cycle within a SHED chamber, wherein the temperature within the fuel tank is thereby determined using a sensor disposed in the fuel tank. The temperature profile determined and recorded in this way fully takes into account the installation situation of the fuel tank in the motor vehicle. Using this temperature profile, according to the invention a theoretical volume of hydrocarbon vapor is determined for each temperature change within a temperature cycle. Instead of a theoretical calculation of the volume of the hydrocarbon vapor for each temperature change within a temperature cycle, it can also be provided that said volume of hydrocarbon vapor is determined empirically for each temperature change and to use the empirically determined variables during the evaporation and the charging of the fuel vapor filter.

The corresponding quantity of hydrocarbon vapor is then produced with an evaporator and a fuel vapor filter is charged with said volumetric flow and discharged, wherein the fuel vapor filter is disposed in a heatable container, which is heated to the target temperature during charging and is cooled to the initial temperature during discharging.

It is particularly advantageous with such an arrangement that a fuel vapor filter can be subjected to the temperature cycle in a relatively small oven with low control inertia. With such a test arrangement a fuel evaporator with a charging pump is the substitute system for the fuel tank that is otherwise to be heated in the SHED chamber. The cooling process is simulated by suitable back flushing.

In this way, it is possible to carry out one or a plurality of temperature cycles on one or a plurality of fuel vapor filters at relatively low cost and especially with low control inertia and temperature inertia.

Preferably, the charging of the fuel vapor filter takes place by means of an evaporator disposed upstream of the fuel vapor filter and at least one charging pump. E.g. a heated container can be provided as an evaporator, which has a significantly smaller volume than the fuel tank. Said evaporator is preferably directly heated.

Discharging of the fuel vapor filter can take place with at least one flushing pump, which is connected to the atmosphere outlet of the fuel vapor filter.

The hydrocarbon emissions of the fuel vapor filter can e.g. be determined using at least one flame ionization detector or alternatively even gravimetrically. In the latter case it is e.g. possible to deposit the emitted hydrocarbons on hydrocarbon monoliths with a honeycomb structure and to weigh the monoliths.

Advantageously, the charging pump and the flushing air pump are controlled depending on the volumetric flow, so that each has an associated volumetric flow measurement device from which the relevant pump receives a regulation signal and/or a control signal.

A particularly advantageous variant of the method according to the invention is characterized by a parallel arrangement of a plurality of fuel vapor filters, each charged from a common fuel evaporator associated with a plurality of fuel vapor filters. The discharging of the fuel vapor filters disposed in parallel takes place advantageously via a plurality of volume-controlled pumps disposed in parallel, wherein each pump is associated with a fuel vapor filter.

The fuel vapor filters can for example be collectively subjected to the measured temperature cycle in a suitably formed oven. The fuel evaporator and pumps and the measurement system are advantageously disposed outside the evaporator.

According to the invention, furthermore an arrangement is provided for carrying out the method, wherein the arrangement comprises at least one fuel evaporator, at least one charging pump, at least one heatable receiving container for at least one fuel vapor filter, at least one flushing pump for connecting the charging pump and the flushing pump to the fuel vapor filter disposed in the receiving container, a means of volumetric flow dependent control of the charging pump and the flushing pump, a means of temperature control and regulation in the receiving container and a means of detecting the quantity of hydrocarbon in a discharge line or at a discharge port, which communicate with a discharge outlet of the fuel vapor filter.

With an advantageous variant of the arrangement, the receiving container is in the form of an oven. The charging pump and the flushing pump are advantageously each associated with a volumetric flow measurement device. Instead of volumetric flow measurement devices, each of which is associated with the charging pump and the flushing pump, it can also be provided that dosable pumps or dosing pumps are used, which deliver a specifiable volume when driven.

The invention is explained below using two measurement configurations schematically illustrated in the drawings.

In the figures:

FIG. 1 shows a measurement configuration according to the invention in accordance with a first variant and FIG. 2 shows a measurement configuration according to the invention in accordance with a second variant.

According to the invention, it is first of all provided to heat a fuelled motor vehicle in a SHED chamber over a specified time interval of e.g. 12 hours from a starting temperature of e.g. 18.3° C. to a target temperature of 40.6° C. Then the temperature is reduced again from the target temperature to the initial temperature. Said temperatures refer to the temperature inside the SHED chamber. During said cycle, within the fuel tank the actual temperature of the fuel and its actual temperature change over the entire time interval are detected and recorded by means of at least one sensor. A volume of hydrocarbon vapor for a specified fuel volume for the temperature change is calculated using said detected temperature profile. The fuel system is assumed to be unpressurised during this.

At a standard air pressure of 1013 mbar and using an approved fuel of the Carb phase 2 type, the relative proportion of hydrocarbon or the partial pressure component of a hydrocarbon/air volume is given as follows:

$P^{dHC}$,18.3° C.=241 mbar→241/1013=23.8% HC-Volume $P_{dHC}$,40.6° C.=543 mbar→543/1013=53.6% HC-Volume The use of approved fuels is prescribed for conducting SHED tests. Such approved fuels are freely available in the market. The fuel used here is traded under the name "Carb phase 2".

For a given compensating volume/vapor collection chamber the volume of hydrocarbon vapor is related to the respective temperature as follows:

$$V^*_{HC} = V_{KKB-vapor\ chamber} \times \int \frac{\sigma_{HC}}{1-\sigma_{HC}} dV$$

Wherein $\sigma_{HC}$ is the volume concentration of hydrocarbons, $\sigma_{HC,1}$ is the volume concentration of hydrogen at a temperature/state T1 and $\sigma_{HC,2}$ is the volume concentration of the hydrocarbons at a temperature/state T2. $V_{KKB}$ refers to the vapor volume of the plastic fuel tank, wherein the Index KKB means plastic fuel tank and the index HC stands for hydrocarbons. The solution of the integral is as follows:

$$V_{HC} = V_{KKB\text{-}vapor\ volume} \times (\ln(1/1 - \sigma_{HC}) - \sigma_{HC}$$

$$V_{HC} = V_{KKB\text{-}vapor\ volume} \times \{\{\ln[1/(1 - \sigma_{HC,1})] - \sigma_{HC,1}\} - (-\ln[1/(1 - \sigma_{HC,2})] - \sigma_{HC,2})\}\}$$

For a vapor chamber volume of 47 l and a temperature T1 (starting temperature of 18.3° C.) and a temperature T2 of 40.6° C. (target temperature) this gives an air component of 25.18 l (76.2% air) for the initial temperature of 18.3° C. and an air component of 11.17 l (46.4% air) for the target temperature of 40.6° C. This gives the air quantity output as follows:

$$V_{air} = 47\ l \times (76.2\% - 46.4\%) = 14.01\ l$$

In the example described below, a temperature cycle is carried out over a time interval of 12 hours. The actual fuel temperatures determined during the cycle, e.g. for a tank with a vapor chamber of 47 l, were stored as a table. The ambient pressure and the volumetric flows during charging and discharging of the fuel vapor filter as well as the fuel temperature in the evaporator are measured.

A temperature change T1 of 18.3° C. at a temperature T2 of 19.2° C. within one hour give a hydrocarbon partial pressure of 241 mbar for an initial temperature of 18.3° C. and a hydrocarbon partial pressure of 249 mbar for a temperature of 19.2° C. At an ambient pressure of 1013 mbar a partial pressure of air of 772 mbar results at the initial temperature of 18.3° C. and a partial pressure of air of 764 mbar results at the target temperature of 19.2° C.

This results in a volume concentration of air at temperature T1 of 76.2% and at temperature T2 of 75.4%. The necessary quantity of air is thus:

$$V = V_{tank} \times (\sigma 1 - \sigma 2) = 47\ l \times 0.8\% = 0.37\ l$$ in the first hour and thus a volumetric flow of 6.2 ml/min (or 8.8 ml/min hydrocarbon-air mixture).

At this point it should be stated that the calculation of the volume of hydrocarbon does not necessarily have to be carried out by integration, rather this can also take place incrementally, as was carried out in the previous specific example.

The measurement configuration 1 illustrated in FIG. 1 is operated with the volumetric flows determined in this way. An evaporator referred to by 2 is in the simplest case in the form of an electrically heated, hermetically sealable vessel.

The evaporator 2 is connected via a charging line 3 to a fuel vapor filter 4, which is disposed within an oven 5. Furthermore, a discharge line 6 is connected to the fuel vapor filter 4 and is connected on the one hand to a measurement device 7 and on the other hand to a flushing pump 8.

A charging pump 9 is connected upstream of the evaporator 2 and the charging pump 9 is controllable for exact dosing by means of a first volumetric flow measurement device 10a, the flushing pump 8 is likewise controllable depending on volumetric flow by means of a second volumetric flow measurement device 10b.

A hydrocarbon-air mixture is now output by the charging pump 9 with a volumetric flow of 8.8 ml/min over a time interval of 1 hour to the fuel vapor filter disposed in the oven 5, wherein the oven 5 is raised within the same time (1 hour) from an initial temperature of 18.3° C. to a temperature of 19.2° C. The valve V1 provided in the charging line 3 is thereby opened and the valve V3 provided in the discharge line 6, which forms the outlet to the measurement device 7, is likewise opened.

The above numerical example relates only to a cycle of 1 hour; in fact the entire cycle from an initial temperature of 18.3° C. to a target temperature of 40.6° C. and back to the initial temperature of 18.3° C. is carried out within a time window of 24 hours, 12 hours being for heating and 12 hours being for cooling. The previously described cycle is repeated for a filter two to three times. Until reaching the target temperature of 40.6° C., the fuel in the evaporator 2 is evaporated and the charging pump 9 continually charges the fuel vapor filter. During this time the bleed measurement takes place by means of the measurement device 7, which can for example be in the form of a flame ionization detector.

After reaching the target temperature, the valves V1 and V3 are closed, a valve V2 is opened to the atmosphere and a valve V4 in a flushing air line 11 is likewise opened. Then the flushing pump 8 is operated until the entire charge volume has been returned via the fuel vapor filter 4. The flushing volume corresponds to the charge volume and the flushing pump is controlled for accurate dosing by means of the volumetric flow measurement devices 10b.

After carrying out such a cycle it may then be possible to run one or a plurality of further measurement cycles.

The temperature profile on the fuel tank obtained in the installation situation only has to be determined once for a fuel tank and a vehicle of a given type, whereas the measurements on the fuel vapor filter can be carried out with diverse, suitably conditioned fuel vapor filters with the use of the temperature profile that was determined once. New fuel filters are first subjected to ageing and then conditioning. During the ageing the new fuel vapor filters are charged multiple times with a mixture of fuel and nitrogen and are then flushed with air. During the conditioning the filter is charged with butane until breakthrough and then flushed.

FIG. 2 shows a measurement arrangement 1 corresponding to that in FIG. 1, wherein the same components are provided with the same reference characters. The measurement arrangement 1 according to FIG. 2 differs from that in FIG. 1 in that a single evaporator 2 is associated with each of a plurality of fuel vapor filters 4 disposed in an oven 5. A charging pump 9 is associated with each fuel vapor filter 4 and is connected via a separate charging line 3 to the fuel vapor filter 4. Furthermore, a flushing pump 8 is associated with each fuel vapor filter 4. With such a measurement arrangement, a plurality of fuel vapor filters 4 can be subjected to a parallel test cycle.

LIST OF REFERENCE CHARACTERS 1 measurement arrangement
2 evaporator
3 charging line
4 fuel vapor filter
5 oven
6 discharge line
7 measurement device
8 flushing pump
9 charging pump
10a, 10b volumetric flow measurement devices
11 flushing air line

The invention claimed is:
1. A method for determining the retention capacity of fuel vapor filters for motor vehicles, comprising the following process steps:
    a) Disposing an at least partly fueled motor vehicle in a heatable test environment, b) Heating and/or cooling the test environment of the motor vehicle from a specified initial temperature to a specified target tem- perature during a specified time interval, c) Measuring the fuel temperature during the heating and/or cooling and determining and recording a temperature profile, d) Calculating a theoretical volume of hydrocarbon vapor based on the temperature profile over the entire temperature cycle according to step b) or taking as a basis an empirically determined volume of hydrocarbon vapor based on the temperature profile over the entire temperature cycle according to step b), e) Evaporating a volume of fuel, f) Disposing at least one fuel vapor filter conditioned for test purposes in a heatable container, g) Heating the container to the target temperature from step b) whilst at the same time charging the fuel vapor filter with the calculated volume of hydrocarbon vapor until reaching the volume of hydrocarbon vapor calculated according to step d) or the empirically determined volume of hydrocarbon vapor according to step d), h) Cooling the container to the initial temperature whilst discharging the fuel vapor filter with a volumetric flow of flushing air, which corresponds to the charging volumetric flow according to step g), and i) Determining the hydrocarbon emissions at the outlet of the fuel vapor filter during charging.

2. The method as claimed in claim 1, characterized in that the charging of the fuel vapor filter is performed be means of at least one evaporator connected upstream of the fuel vapor filter an at least one charging pump.

3. The method as claimed in claim 2, characterized in that the discharging of the fuel vapor is performed by means of at least one flushing pump, which is connected to an atmosphere outlet of the fuel vapor filter.

4. The method as claimed in claim 3, characterized in that the charging pump and the flushing air pump are controlled depending on volume.

5. The method as claimed in claim 1, characterized in that the hydrocarbon emissions of the fuel vapor filter are determined by means of at least one flame ionization detector.

6. The method as claimed in claim 1, characterized in that the hydrocarbon emissions of the fuel vapor filter are determined gravimetrically.

7. The method as claimed in claim 1, characterized by a parallel arrangement of a plurality of fuel vapor filters, each charged by a common fuel evaporator associated with the plurality of fuel vapor filters.

8. The method as claimed in claim 1, characterized in that the temperature of the fuel for a fuel tank that is unpressurized compared to the test environment is measured by means of at least one sensor disposed within the fuel tank.

9. The method of claim 1 further including repeating process steps g) through i).

10. A measurement arrangement for carrying out the method as claimed in claim 1, comprising at least one fuel evaporator, at least one charging pump, at least one heatable receiving container for at least one fuel vapor filter, at least one flushing pump, the charging pump and the flushing pump connected to the fuel vapor filter disposed in the receiving container, a means of volumetric flow dependent control for the charging pump and the flushing pump, a means of temperature control and regulation in the receiving container and a means of detecting the quantity of hydrocarbons in a discharge line or at a venting port, which communicate with a discharge outlet of the fuel vapor filter.

11. The arrangement as claimed in claim 10, characterized in that the receiving container is in the form of an oven.

12. The arrangement as claimed in claim 10, characterized in that both the charging pump and also the flushing pump are each associated with a volumetric flow measurement device.

13. The arrangement as claimed in claim 10, characterized in that the charging pump and/or the flushing pump are configured to deliver a controllable predetermined volumetric flow.

* * * * *